United States Patent [19]

Ford

[11] Patent Number: 5,466,463
[45] Date of Patent: Nov. 14, 1995

[54] VIRACIDAL, BACTERICIDAL AND SPERMICIDAL VAGINAL SUPPOSITORY

[75] Inventor: Larry C. Ford, Irvine, Calif.

[73] Assignee: Lafor Laboratories Limited, Newport Beach, Calif.

[21] Appl. No.: 301,966

[22] Filed: Sep. 7, 1994

Related U.S. Application Data

[63] Continuation-in-part of Ser. No. 161,659, Dec. 3, 1993, abandoned.

[51] Int. Cl.$^6$ .............................. A61F 13/20; A61F 6/08; C12N 11/04
[52] U.S. Cl. ................................. 424/433; 424/DIG. 15; 514/967; 435/853; 435/854
[58] Field of Search .......................... 424/433, DIG. 15, 424/451; 514/967; 435/853, 854

[56] References Cited

U.S. PATENT DOCUMENTS

| | | | |
|---|---|---|---|
| 4,579,734 | 4/1986 | Hata et al. | 435/853 |
| 4,983,163 | 1/1991 | Winans, Jr. et al. | 435/854 |

FOREIGN PATENT DOCUMENTS

| | | |
|---|---|---|
| 0047609 | 9/1976 | Netherlands . |

OTHER PUBLICATIONS

Monif, Gilles R. G. et al. "Quantitative and qulitative effects of povidone–iodine liquid and gel on the aerobic and anaerobic flora of the female genital tract", *Am.J. Obstet. Gynecol.* 137(4): 432–438 (Jun. 15, 1980).

McGroarty, Jacqueline A. et al. "Development of Lactobacillus Probiotics", *Clinical Advances in the Treatment of Infections*, New York, pp. 16, 13–14.

McGroarty, Jacqueline A. and Moody, Karen J., "nonoxynol–9 and Urogenital Infections in Women", *Clinical Advances in the Treatment of Infections*, p. 16, 12–14.

Sherris, Jacqueline D. et al. "New Developments in Vaginal Contraception", Population Reports, (By Population Information Program, The Johns Hopkins University), 12(1): H–159–191 (1984).

McGroarty, Jacqueline A. et al. "Influence of the spermicidal compound Nonoxynol–9 on the growth and Adhesion of Urogenital bacteria in vitro", *Current Microbiology*, vol. 21 (1990), 219–223.

McGroarty, Jacqueline A. et al. "Hydrogen Peroxide Production by Lactobaillus Species: Correlation with Susceptibility to the Spermicidal Compound Nonoxyno–9", *JID*, 1992:165 (Jun.), 1142–1144.

McGroarty, J. A. et al. "Influence of the Spermicidal Compound Nonoxynol–9 on the Adhesion of E coli to Human Epithelial Cells", *Int Urogynecol J*, (1993)4: 194–198.

McGroarty, J. A. et al. "Modulation of Adhesion of Uropathogenic Enterococcus faecalis to Human Epithelia Cells in vitro by Lactobacillus species", *Microbial Ecology in Health and Disease*, vol. 5: 309–314(1992).

McGroarty, Jacqueline A. et al. "The Spermicidal Compound Nonoxynol–9 Increases Adhesion of Candida Species to Human Epithelial Cells in Vitro", *Infection and Immunity*, 58(6): pp. 2005–2007, (Jun., 1990).

Kreiss, Joan et al. "Efficacy of Nonoxynol 9 Contraceptive Sponge Use in Preventing Heterosexual Acquisition of HIV in Nairobi Prostitutes", *JAMA*, Jul. 22/29, 1992, 268(4): 447–482.

Goldin, Barry R. and Gorbach, Sherwood L. "Alterations of the Intestinal Microflora by Diet, Oral Antibiotics, and Lactobacillus: Decreased Production of Free Amines From Aromatic Nitro Compounds, Azo Dyes, and Glucuronides", *JNCI*, 73(3): 689–695(Sep. 1984).

Barefoot, Susan F. and Klaenhammer, Todd R. "Detection and Activity of Lactacin B, a Bacteriocin Produced by Lactosbacillus acidophilus", *Applied and Environmental Microbiology*, 45(6):1808–1815(Jun., 1983).

Barefoot, Susan F. and Klaenhammer, Todd R. "Purification and Characterization of the Lactobacillus acidophilus Bacteriocin Lactacin B", *Antimicrobial Agents and Chemotherapy*, 26(3): pp. 328–334 (Sep. 1984).

Mehta, A. M. et al. "Purification and properties of the inhibitory protein isolated from Lactobacillus acidophilus AC", *Microbios*, 38: pp. 73–81(1983).

Silva, M. et al. "Antimicrobial Substance from a Human Lactobacillus Strain", *Antimicrobial Agents and Chemotherapy*, 31(8): pp. 1231–1233(Aug. 1987).

S. Leodolter, E. Reinhold et al. "Ceftriaxon, I g i.v.–Effectively Prevents Infections and Is Cost Effective", *Program And Abstras–3rd World Congress for Infectious Diseases in Obstetrics and Gynecology combined with Infectious Diseases in Urology, Dermatology, and Clinical Immunology*, Acapulco, Mex., 1993. p. 110.

Ford, L. C. et al. "In Vitro Antimicrobial Effects of the Inner Confidence Lactobacilli (Lactobacillus Acidophilus 6 Lactobacillus Rhamnosus)" *Program And Abstrats–3rd World Congress for Infectious Diseases in Obstretrics and Gynecology combined with Infectious Diseases in Urology, Dermatology and Clinical Immunology*, Acapulco, Mex., 1993, p. 110.

(List continued on next page.)

Primary Examiner—Carlos A. Azpuru
Attorney, Agent, or Firm—Klein & Szekeres

[57] ABSTRACT

A vaginal suppository or other type of vaginal pessary such as cream, foam or ointment, which contains as its active ingredients at least one pharmaceutically acceptable, topically safe antimicrobial agent, such as an agent selected from the group of benzalkonium chloride, cetylpyridinium chloride, chlorhexidine gluconate and povidone iodine, imidiazolidinyl urea and diazolidinyl urea and a viable colony of micro-encapsulated lactobacilli bacteria. The viable lactobacilli are included in the suppository in micro encapsulated form, which protects the bacteria during storage of the suppository from the action of the bacteriocidal agent. When exposed to the vaginal milieu the micro encapsulation breaks down sufficiently to release the lactobacili bacteria. The lactobacilli bacteria serve to maintain or re-establish a healthy lactobacilli based flora on the vaginal wall, and excrete hydrogen peroxide and other bactericidins which suppress abnormal flora conditions that promote infections.

35 Claims, No Drawings

OTHER PUBLICATIONS

Ford, L. C. et al. "Safety of Inner Confidence Supporitories", *Proram And Abstracts–3rd World Congress for Infectious Diseases in Obstetrics and Gynecology combined with Infectious Diseases in Urology, Dermatology and Clinical Immunology,* Acapulco, Mex., 1993, p. 111.

Ford, L. C. et al. "Topical Therapy of Bacterial Vaginosis", *Program and Abstracts–1st World Congress for Infectious Diseases in Obstetrics and Gynecology,* Hawaii, USA, 1989, p. 78.

VIRACIDAL, BACTERICIDAL AND SPERMICIDAL VAGINAL SUPPOSITORY

CROSS REFERENCE TO RELATED APPLICATION

The present application is a continuation-in-part of application Ser. No. 08/161,659, filed Dec. 3, 1993 now abandoned.

BACKGROUND OF THE INVENTION

1. Field of the Invention

The present invention is in the field of bactericidal, viracidal and spermicidal materials. More specifically, the present invention is directed to a vaginal suppository which is spermicidal and is highly effective for preventing the transmission of sexually transmitted diseases during heterosexual intercourse.

2. Brief Description of the Prior Art

Spermicidal agents, such as nonoxynol 9 or oxtoxynol 9 have been widely used in the prior art in suppositories, creams, foams by themselves and also in conjunction with various mechanical contraceptive devices, primarily for the purpose of contraception. Nonoxynol 9 has also been reported in the prior art to have certain bacteriocidal action and capable of killing the human immunodeficiency virus (HIV), at least in certain in vitro tests. The use of nonoxynol 9 (or of octoxynol 9), and other spermicidal and bacteriocidal agents in vaginally inserted suppositories, creams, foams or the like, however, is not without problems inasmuch as these agents tend to diminish or destroy the healthy bacterial flora of the vagina, and cause for the woman a tendency to develop yeast infections (candidasis).

In light of the foregoing, there has always existed a need in the art for a contraceptive agent which can be used by a woman intra-vaginally before sexual intercourse, and which is highly effective as a contraceptive, and perhaps even more importantly as an agent for preventing transmission of the numerous sexually transmitted diseases. The need for such a contraceptive and prophylactic agent has increased even further since the appearance and spread of the HIV virus in the general heterosexual population. Moreover, there is a need in the art for a contraceptive and prophylactic agent which diminishes the likelihood for its female user to develop yeast infections. Although the prior art has recognized the need to maintain or re-establish a healthy intravaginal bacterial flora, the only solution provided to this problem in the prior art was in the form of douches or other types of vaginal inserts which contained a colony of *Lactobacillus acidophilus*. These douches or other inserts are, however, less than 100% effective, and also they contribute nothing to contraception, nor do they protect against transmission of sexually transmitted diseases during heterosexual intercourse.

The present invention provides a vaginal suppository which not only helps to maintain or re-establish a normal non-pathogenic intra-vaginal bacterial flora but is also contraceptive and provides substantial protection against transmission of sexually transmitted diseases.

SUMMARY OF THE INVENTION

It is an object of the present invention to provide a vaginal suppository which is highly efficacious to prevent transmission of virtually all sexually transmittable diseases and also acts as a contraceptive agent.

It is another object of the present invention to provide a vaginal suppository which meets the foregoing objectives, and does not render its user susceptible to yeast infections.

The foregoing and other objects and advantages are attained by a vaginal suppository or other type of vaginal pessary such as cream, foam or ointment, which contains as its active ingredients:

at least one pharmaceutically acceptable, topically safe antimicrobial agent, such as an agent selected from the group of benzalkonium chloride, cetylpyridinium chloride, chlorhexidine gluconate and povidone idone, imidazolidinyl urea and diazolidinyl urea;

and a viable colony of micro-encapsulated lactobacilli bacteria.

The viable lactobacilli are included in the suppository in micro encapsulated form, which protects the bacteria during the "shelf-life" of the suppository from the action of the antimicrobial agent. The coating or substance which encapsulates the bacteria on the other hand is of such material which releases the bacteria in the vaginal milieu primarily due to the effect of moisture. The released lactobacilli bacteria serve to maintain or re-establish a healthy lactobacilli based flora on the vaginal wall, and excrete hydrogen peroxide and other bactericidins which suppress abnormal flora conditions that promote infections.

The preferred embodiments of the invention comprise in addition to micro encapsulated lactobacilli bacteria a combination of antimicrobial (bacteriocidal) agents, such as at least one agent selected from the group of benzalkonium chloride, cetylpyridinium chloride, chlorhexidine gluconate and povidone iodine (BETADINE™) and additionally imidazolidinyl urea and diazolidinyl urea; and also a spermicidal agent selected from nonoxynol 9 or octoxynol 9, and still further a buffer using a mild acid such as boric acid or an organic acid such as lactic acid, citric acid or acetic acid to achieve a mildly acidic pH in the range of 3.0 to 5.5 in the suppository, cream foam or ointment and after use in the vaginal wall.

In vitro and in many cases also in vivo tests pertaining to several sexual transmittable pathogens, including *Candida albicans* and related yeast species, *Trichomonas vaginalis, Neisseria gonorrhoeae, Treponema pallidum, Chlamydia trachomatis, Herpes simplex* and the Human Immunodeficiency Virus, have demonstrated that the vaginal suppository of the present invention is highly efficacious in killing the sexually transmittable pathogens, helps to maintain or re-establishes a healthy non-pathogenic bacterial flora in the vagina, and prevents vaginitis and yeast infections. The vaginal suppository of the present invention is also substantially free of untoward side effects (such as burning, itching or other unpleasant sensations) and in the test conducted was generally well accepted by it female user and her partner.

The following is a detailed description of the invention, and a summary of certain tests and results which demonstrated the effectiveness of the invention.

DETAILED DESCRIPTION OF THE INVENTION

A vaginal suppository, cream, foam or ointment is provided in accordance with the present invention which contains a unique combination of an antimicrobial agent combined with viable micro-encapsulated *Lactobacillus acidophilus* bacteria. The bacteria are microencapsulated to protect them from the action of the antimicrobial agent.

Generally speaking, the object of the present invention can be attained by a vaginal cream, foam, or ointment, but the preferred embodiment is in the form of a suppository, and the invention is further described with reference to a suppository. It should be understood however, that the generic principles of the present invention can also be embodied and incorporated in the above-mentioned creams, foams or ointments, which together with the suppository can be commonly referred to as "vaginal pessary" or "pessaries".

The antimicrobial (bacteriocidal) agent incorporated in the suppository in accordance with the present invention can be any pharmaceutically acceptable, topically safe antimicrobial agent known in the art. Examples are cationic surfactant type antimicrobial (bacteriocidal) agents such as benzalkonium chloride, methylbenzethonium chloride, cetyl pyridinium chloride and cetrimide (mixed alkyltrimethylammonium bromides). Alternatively the bacteriocidal agent can be chlorhexidine gluconate or an iodine containing bacteriocidal agent, such as povidone iodine (commonly known under the brand name BETADINE™). In accordance with the invention approximately 12 to 3000 mg benzalkonium chloride or methylbenzethonium chloride is present in each vaginal suppository, the preferred amount being approximately 120 mg of benzalkonium chloride per suppository. It is to be understood in this regard that in accordance with the present invention a female user of the invention is to apply intra-vaginally one suppository a few minutes to a few hours before sexual intercourse. The total weight of the preferred embodiment of the suppository is approximately 1.2 grams (1200 mg), however this should not be construed as a limitation inasmuch as the total weight and volume of the suppository depends not only on the amount of active ingredients but also on the amount of inactive ingredient (filling agents, pharmaceutical excipients) which are contained in the suppository. In the following description, whenever the preferred amount of an ingredient or component is stated, this should be understood to apply as "per one suppository", which in the preferred embodiment weighs approximately 1.2 grams.

In accordance with the invention cetylpyridinium chloride is used in the range of 25 to 4000 mg per suppository, the preferred amount being in the range of 50 to 1000 mg. Chlorhexidine gluconate is used in the range of 10 to 2000 mg, the preferred range being 25 to 1200 mg. Povidone iodine (BETADINE™) is used in the range of 25 to 5000 mg, the preferred amount being about 120 mg per suppository. In the preferred embodiments one of the above noted antimicrobial agents is selected in the above-mentioned amounts, however a combination of these agents, in equivalent amounts, can also be used. In addition to being a bacteriocidal agent, the cationic surfactant type agents such as benzalkonium chloride also have spermicidal effect.

Still further bacteriocidal agents which can be utilized in the present invention is imidiazolidinyl urea, which is used in the range of 10 to 1000 mg per suppository, the preferred amount being approximately 100 mg.

Diazolidinyl urea, can be used in the range of 10 to 1000 mg per suppository, the preferred amount being approximately 100 mg. Still additional examples of antimicrobial agents which can be used in the present invention are hexylresorcinol (25 to 1000 mg), cetrimide (100 to 4000 mg), hexachlorophene (25 to 3000 mg), triclocarban (3,4'4'-trichlorocarbanilide 50 to 1000 mg), chloroxylenol (25 to 1000 mg) and hexadecyltrimethylammonium bromide (25 to 400 mg).

Among the foregoing antimicrobial agents, benzalkonium chloride is the most preferred, particularly in embodiments where only one antimicrobial agent is utilized.

In preferred embodiments of the invention, however, not one, but rather a combination of antimicrobial agents are utilized.

A particularly preferred type of embodiment contains one antimicrobial agent selected from the group consisting of benzalkonium chloride, methylbenzethonium chloride, cetyl pyridinium chloride, chlorhexidine gluconate and povidone iodine (BETADINE™). This type of preferred embodiment also contains imidiazolidinyl urea, and diazolidinyl urea.

Another essential component of the vaginal suppository of the present invention is a viable colony of *Lactobacillus acidophilus* or of *Lactobacillus rhamnosus* bacteria, which should be present in the range of $10^3$ to $10^7$ viable bacteria per suppository, a more preferred range being $10^5$ to $10^7$, and the preferred number of viable bacteria being approximately 1 million ($10^6$) per suppository. The bacteria are contained in the suppository in a micro encapsulated form. In the preferred embodiment the bacteria are of the *Lactobacillus rhamnosus* species, and each suppository contains at least approximately $10^6$ viable bacteria. Although some bacteriologists may consider *Lactobacillus rhamnosus* as a separate but related species to *Lactobacillus acidophilus*, rhamnosus is more properly considered a simple variant of the acidophilus species. As is known in the art, both *Lactobacillus acidophilus* and *Lactobacillus rhamnosus* are "friendly" bacteria, and form a healthy intra-vaginal bacterial flora. Both of these bacteria are known to produce certain bactericidins and hydrogen peroxide, which helps to suppress pathogenic bacteria. The advantage of *Lactobacillus rhamnosus* over the acidophilus variant in the present invention is in the facts that the rhamnosus variant is more prolific (about 8 to 10 times), and is capable of fermenting more carbohydrates (23 compared to 12 of the acidophilus variant) and that the rhamnosus variant produces $L^+$ lactic acid instead of a racemic mixture of lactic acid produced by the acidophilus variant. The foregoing are advantageous because the rhamnosus variant's ability to ferment more types of carbohydrates makes it a more sturdy, survival-prone bacteria. Production of $L^+$ lactic acid is advantageous because it is the $L^+$ enantiomer which has substantial anti-fungal action.

Both the *Lactobacillus acidophilus* and *Lactobacillus rhamnosus* variant bacteria used in the present invention can be purchased from commercial sources, or can be obtained from laboratory strains. The *Lactobacillus rhamnosus* variant used in the below described preferred embodiment is obtained from the Institute Rosell Montreal, Quebec Canada. The Lactobacillus variant is micro encapsulated in accordance with the present invention, and is admixed with the antimicrobial agent or agents and other components of the invention in the micro encapsulated form. Several methods or procedures for micro encapsulating these bacteria are described below. The purpose of micro encapsulating the bacteria is to protect them from the action of the antimicrobial agent (or agents) before the suppository is used. The material or coating which encapsulates the bacteria is selected in such a manner in accordance with the present invention that the material loses its structural integrity as a film in the vaginal environment (primarily due to moisture) and releases the lactobacilli bacteria.

In addition to the bacteriocidal agent or agents and micro encapsulated lactobacillus bacteria, the suppository of the present invention also contains the following non-essential ingredients or components. These components are considered non-essential because the basic objectives of the invention can be attained without them. Nevertheless, the embodiments of the invention which include these non-essential components offer certain advantages, and are therefore considered the preferred embodiments, and should also be considered novel and innovative, in their combination, to the basic embodiments.

Thus, the preferred embodiments of the suppository of the present invention contain a primary spermicidal agent selected from nonoxynol 9, or octoxynol 9. The latter is considered substantially equivalent with nonoxynol 9 for the purposes of the present invention. Each suppository contains nonoxynol 9 in the range of approximately 50 to 500 mg, the preferred amount being 100 mg. The use of nonoxynol 9 in accordance with the prior art has certain serious disadvantages in that repeated use increases the likelihood of vaginitis and yeast infection, primarily because nonoxynol 9 tends to adversely affect the normal bacterial flora of the vagina. However, the use of nonoxynol 9 in combination with the other components in accordance with the present invention does not have these disadvantages.

The preferred embodiments of the vaginal suppository of the present invention also contain a buffering agent capable of buffering the suppository and capable of maintaining for several hours after sexual intercourse, an intra-vaginal pH of approximately 3.0 to 5.5, preferably a pH of 4.3 to 4.5. Any mild pharmaceutically acceptable acid, such as boric acid, or mild organic acids such as lactic acid, ascorbic acid, citric acid, or acetic acid, in combination with the respective sodium or other pharmaceutically acceptable salt (to the extent necessary to achieve the desired pH) can be used. Preferably, the pH of the suppository is buffered in the range of 4.3 to 4.5, and preferably lactic acid with sodium lactate or a combination lactic acid/sodium lactate and ascorbic acid are used for buffering.

It has been found in accordance with the present invention that the suppository buffered in the above-described manner actually allows the vaginal pH to remain acidic post-coitally, which is known to be advantageous for contraception and also for maintenance of a healthy vaginal bacterial flora. The use of ascorbic acid as part of the buffering system is advantageous for the additional reason that ascorbic acid has been shown to increase the viscosity of cervical mucus and thereby make it more difficult for either sperm or microorganisms to enter the cervix. Thus, ascorbic acid contributes to both the antimicrobial and contraceptive effects of the suppository of the present invention.

The suppository of the present invention also contains such pharmaceutical excipients which make suppository formation possible. Hydroxy propyl methyl cellulose (approximately 40 grams per 100 suppositories) and microcrystalline cellulose (approximately 20 grams per 100 suppositories) are particularly advantageous because these ingredients adhere well to the vaginal wall in an acidic environment which is secured by the inclusion of the appropriate buffer system in the suppository of the invention. Further excipients such as magnesium stearate (2–4 grams per 100 suppositories) and silicon dioxide (2–4 grams per 100 suppositories) and lactose ((2–3 grams per 100 suppositories) are also included in the preferred embodiments.

Still further optional components or ingredients which may be included in the suppository of the present invention are fragrances; menthol, eucalyptus oil, methyl salicylate or related salicylates as topical cooling agents; hydrocortizone or related antiinflammatory steroids (1 to 500 mg per suppository) as anti-inflammatory agents; EDTA as a wetting agent and mild antimicrobial; propylene glycol or other pharmaceutically acceptable glycols, methyl paraben or related paraben derivatives as wetting agents and for "texture"; para diisobutylphenoxy polyethoxyethanol or dodoecaethylene glycol monolaurate as spermicidal and mild antimicrobial agents; tritions and menfegol as spermicidal, mild antimicrobial and wetting agents.

In the following description the applicant first describes actual examples of procedures for micro encapsulating *Lactobacillus acidophilus* or *Lactobacillus rhamnosus* bacteria, and actual examples of preferred embodiments of the suppository of the present invention.

Specific Examples

ENCAPSULATION METHODS:

Viable, lyophilized lactobacilli bacteria that have been lyophilized after the removal of the media are used for encapsulation. The bacteria can be obtained from commercial sources, or can be obtained from laboratory strains. In the currently preferred embodiments *lactobacillus rhamnosus* bacteria are purchased from Institute Rosell Montreal, Quebec, Canada. The organisms are grown to log phase in nutrient media. Suitable media include Thayer-Martin media, Trypticase Soy, Brain-Heart Infusion Broth, or any other enriched media suitable for the cultivation of these organisms, as no particular media is critical to the success of this suppository. The only important factors are the viability and quantity of the micro-organisms that are always determined by standard clinical laboratory dilution methods, such as plating the quantified dilution of bacteria on to blood agar plates or other enriched media, incubating at 37 degrees C. for 24–48 hours in a 5–10% carbon dioxide atmosphere, and then performing a colony count. The removal of the nutrient media is done by centrifugation at 14,000×g at 0°–4° C., and then washing with sterile, balanced salts and 5% glucose solution at least three times after the initial centrifugation. The bacteria are then "snap frozen" with liquid nitrogen and then lyophilized under high vacuum.

ENCAPSULATION METHOD A:

The freshly obtained, washed and lyophilized bacteria obtained as described above are suspended in 10 ml of 5% glucose saline solution in such volume so as to obtain a heavy suspension of bacteria which contains between one to ten billion organisms per ml, at 0–4 degrees C. All of these procedures are performed in the 0–4 degrees C. temperature range unless otherwise noted, in order to maintain viability of the lactobacilli bacteria which at room temperature lose viability. The suspension of bacteria is rapidly, but gently, stirred while 0.2–0.4 ml of sodium alginate solution (1.5% weight by volume) is added. The above mixture is then transferred into a 4 liter round bottom flask by using a nitrogen stream through a sheathed 14 gauge needle. The 4 liter round bottom flask was previously washed with a 5% albumin solution, and thereafter heated for at least 10 hours at 65 degrees C., and the needle and the tubing used in the process have also been treated this way.

Thereafter the above mixture is forced through a 30 gauge multi-beveled needle under pressure using a large syringe and nitrogen stream. Very small droplets are generated at the end of the needle which are dried by the nitrogen and air stream around the 30 gauge needle, and the droplets are collected in an aqueous solution of 1.3–2% calcium chloride where they gel. Thereafter, they are washed at least three times with 0.08–0.13% 2-(N-cyclohexyl-amino) ethanesulfonic acid (CHES) solution and 1.0–1.5% calcium chloride solution.

The gelled droplets or little spheres are further washed with at least a five fold excess of the 0.1% CHES 1.1% calcium chloride, and normal saline solution. The resultant spheres are then "snap frozen" in liquid nitrogen and then lyophilized. After these steps, the encapsulated organisms can be used in the formulations of the present invention.

ENCAPSULATION METHOD B:

As an improvement over Encapsulation Method A, the following further steps are performed to render the bacteria more resistant to the cationic antimicrobials. The steps are performed at 0–4 degrees C. Thus, after the washings described in Encapsulation Method A the materials are reacted with poly L- lysine (Sigma) solution (0.05% w/v) spheres for ten minutes. The spheres are then washed with normal saline buffered to pH 4.5 with lactic acid. The resultant spheres are then "snap frozen" in liquid nitrogen and then lyophilized. After these steps, the encapsulated organisms can be used in the formulations of the present invention.

ENCAPSULATION METHOD C:

At 0–4 degrees C., the freshly obtained, washed, lyophilized bacteria are mixed with hydroxypropylmethylcellulose to achieve a weight to weight ratio of bacteria to the hydroxypropylmethylcellulose of 10/90, although the range can vary from 1/99 to 99/1, respectively. This will effect the final mass and viability of encapsulated organisms. It should be understood that higher ratios of cellulose tend to "protect" the bacteria in the encapsulation process. The mixture of lyophilized bacteria and hydroxypropyl methylcellulose is encapsulated by "pan" coating. This is done by using a stainless steel round bottom flask which first had been "coated" with about 1% magnesium stearate, suspension in water. A combination of a freely water permeable acrylic methacrylic acid ester copolymer and a partially water permeable acrylic methacrylic acid ester copolymer, (EUDRAGIT RL™ and EUDRAGIT RS™, respectively (obtained from Rohm Parm. Ltd., Germany) is suspended at 5–10% concentration in acetone-isopropanol, 1:1, containing a 1% w/v of castor oil. The ratio of the two copolymers can vary from 1:1 to 1:10, with a preferred ratio of 1:2. The suspension is contained in the stainless steel round bottom flask. As the suspension of the copolymer kills bacteria rapidly, the process has to be performed rapidly with a high ratio of the hydroxypropylmethyl cellulose to bacteria. Thus, the mixtures of bacteria and cellulose are added to the stainless steel flask in small amounts, agitating vigorously for 3–10 minutes while the material is being dried over a nitrogen stream.

ENCAPSULATION METHOD D:

The freshly obtained, washed, lyophilized bacteria are added using rapid, but gentle stirring at 0–4 degrees C., to a thick suspension of polyvinylpyrrolidone (commercially available BASF, Germany) which may or may not be crosslinked, for 2 to 12 hours with a one percent (1%) solution of divinylbenzene (Biorad) in a 5% glucose balanced salts solution at a pH of 5.0 (range 4.5–8.0). The lactobacilli become encapsulated by stirring in this mixture for 1–12 hours. The material is then "snap frozen" and lyophilized.

ENCAPSULATION METHOD E:

The freshly obtained, washed, lyophilized bacteria are added using rapid, but gentle stirring to a suspension of polyvinylpovidone (Crospovidone™). Specifically, ten grams of lyophilized bacteria are added to a suspension of 50 gm of polyvinylpovidone (Crospovidone™) at 0–4 degrees C. The encapsulation occurs by stirring for 30–60 minutes, although longer times can be used. Moisture is then removed from the mixture with a vacuum in a desiccator, or the material is "snap frozen" and lyophilized.

SUPPOSITORY FORMULATION METHOD A:

The Benzalkonium Chloride or methylbenzethonium chloride (12.5 grams for a batch of 100 suppositories) imidiazolidinyl urea (11 grams for a batch of 100 suppositories) and diazolidinyl urea (1.1 grams for a batch of 100 suppositories, or alternatively 1.1 grams of diazolidinyl urea and 1.1 g of imidiazolidinyl urea to achieve a tenfold lesser concentration) are added slowly while thoroughly stirring, to a suspension of hydroxypropyl methyl cellulose (40 grams per batch of about 100 suppositories) and microcrystalline cellulose (20 grams per batch of about 100 suppositories) in a sterile normal saline solution (quantity sufficient to a make a thick paste, usually 120 ml) at 35–37 degrees C. The pH is slowly lowered to about 6.0–6.3 with reagent grade lactic acid. (This step binds the antimicrobials to the "cellulose" excipients.) The suspension is stirred for two hours, then 10.0 grams of ascorbic acid which were dissolved in about 10–15 ml of sterile saline are slowly added with gentle stirring. The material is, at this point, a very thick paste. Spermicide (11 grams of Nonoxynol 9 for a batch of 100 suppositories) is now added and thoroughly mixed. After this step the process is performed at 0–4 degrees C. The pH of the mixture is then lowered to 4.3–4.5 with reagent grade lactic acid. Then freshly obtained encapsulated lactobacilli bacteria are added to achieve a final concentration of at least one million viable bacteria per suppository. Inasmuch as the goal is to achieve a final concentration of at least one million viable bacteria per suppository, a 4– 6 fold excess of bacteria are usually added, because some loss of the viability occurs during the various mixing processes. This means that about 500 mg of the encapsulated bacteria are usually added. It is important to mix these organisms not only thoroughly to ensure uniformity, but also quickly because moisture adversely effects the viability of the organisms. Rapid and thorough mixing, can be done, for example, by spreading the paste in a thin layer on a sterile glass plate and then using a replicator to spread the bacteria evenly over the paste. Thereafter, for a batch of 100 suppositories, about 2–4 grams each, of magnesium stearate and silicon dioxide are added, with or without 2–3 grams of lactose.

After the materials are thoroughly mixed at 0–4 degrees C. they are pressed into a mold and dried in a desiccating jar under vacuum at 0–4 degrees C. (Drying at room temperature (25 degrees) or at higher temperatures, decreases the number of viable bacteria.) The suppositories are then sealed in air and moisture proof containers, until used. During storage they should be protected from moisture and extreme temperatures, to ensure the viability of the lactobacilli.

SUPPOSITORY COMPOSITION B:

The process of making this composition is performed as the process for SUPPOSITORY FORMULATION A, except that cetylpyridinium chloride (12.5 grams for a batch of 100 suppositories) is used instead of benzalkonium chloride.

SUPPOSITORY FORMULATION C:

This formulation is made in substantially the same way as suppository Formulation A, except that instead of benzalkonium chloride, chlorhexidine gluconate (12.5 grams for a batch of 100 suppositories) is used.

SUPPOSITORY FORMULATION D, CONTAINING POVIDONE IODINE (BETADINE™), GLYCEROL BASED.

The composition and process is similar to the one described above for SUPPOSITORY FORMULATION A, with the following differences: Povidone iodine (BETADINE™) (12.5 grams for a batch of 100 suppositories) is used in place of benzalkonium chloride. The three antimicrobial agents (imidiazolidizyl urea 1.1 to 11 grams, diazolidizyl urea 11 to 1.1 grams and povidone iodine) are added slowly while thoroughly stirring to 1L of a suspension of glycerol at a concentration of 20–80%, in sterile 0.15 normal (0.85%) saline solution. The pH is slowly lowered to about 6.0–6.3 with reagent grade lactic acid. This step slightly thickens the mixture.

After the suspension stirs for two hours, 6.0–10 grams of ascorbic acid that was dissolved in about 10–15 ml of sterile saline is slowly added with gentle stirring. The mixture is, at this point, a very thick suspension. The pH of the entire mixture is then lowered to 4.3–4.5 with reagent grade lactic acid. The material is quickly cooled to 0–4 degrees C. while adding the freshly obtained, encapsulated bacteria, as in the previously described processes, but in this process usually about 600–800 mg of the encapsulated bacteria are added and blended in thoroughly, together with 4–6 grams of lactose. Unlike in the previously described processes and composition, no magnesium stearate or silicon dioxide is added. The formulation at this point is quite firm, like a soft wax at 0–4 degrees C. and can be easily pressed into a mold. The resulting suppositories are then sealed in air and moisture proof containers until used. The suppository of this composition melts rapidly at 37° C., and therefore particular care should be exercised to keep it cool during storage and prior to use.

SUPPOSITORY FORMULATION E (GLYCEROL BASED).

Benzalkonium chloride (12.5 grams for a batch of 100 suppositories) imidiazolidinyl urea (11 to 1.1 g) and diazolidinyl urea (11 to 1.1 g) are added slowly while thoroughly stirring, to 1L of a suspension of glycerol at a concentration of 20–80% in sterile 0.15 normal saline solution. The pH is slowly lowered to about 6.0–6.3 with reagent grade lactic acid. This step slightly thickens the mixture. After the suspension stirs for two hours, 6.0–10 grams of ascorbic acid, dissolved in about 10–15 ml of sterile saline, are slowly added with gentle stirring. The mixture is, at this point, a thick viscous suspension, (similar to thick honey in its consistency). 11 grams of Nonoxynol 9, is then added and thoroughly mixed. The pH of the entire mixture is then lowered to 4.3–4.5 with reagent grade lactic acid. The material is quickly cooled to 0–4 degrees C. while adding freshly obtained encapsulated lactobacilli bacteria. Usually about 600–800 mg of the encapsulated bacteria are added and blended in thoroughly together with 4–6 grams of lactose, to obtain a final product which contains at least $10^6$ viable bacteria per suppository. At this stage the formulation is quite firm, like a soft wax at 0–4 degrees C. and can be easily pressed into a mold. The resulting suppositories are then sealed in air and moisture proof wrappings until used. During storage they should be protected from moisture, and particular care should be taken to keep them cool, as the glycerol based suppositories melt at about 37° C.

SUPPOSITORY FORMULATION F (GLYCEROL BASED)

This formulation is made by substantially the same process and has substantially the same components as FORMULATION E, except that instead of benzalkonium chloride cetylpyridinium chloride (12.5 grams for a batch of 100 suppositories) is used.

SUPPOSITORY FORMULATION H (GLYCEROL BASED)

This formulation is made by substantially the same process and has substantially the same components as FORMULATION E, except that instead of benzalkonium chloride chlorhexidine glucoate (12.5 grams for a batch of 100, suppositories) are used.

SUPPOSITORY FORMULATION I (GLYCEROL BASED)

This formulation is made by substantially the same process and has substantially the same components as Formulation E, except that instead of benzalkonium chloride polyvinylpyrrdidone iodine (BETADINE™) (12.5 grams for a batch of 100 suppositories) will be used.

LARGE BATCH FORMULATION (FORMULATION J)

In an alternative "pilot batch" procedure approximately 20,000 suppositories can be made in each run. Sufficient quantities of benzalkonium chloride, imidiazolidinyl urea and diazolidinyl urea to achieve a final amount of approximately 120 to 1000 mg, 10 to 100 mg, and 10 to 100 mg, respectively, per suppository, as desired, are mixed together with sufficient quantities of nonoxynol 9 to achieve a final concentration of 90–110 mg. of the latter in each suppository. The above ingredients are all added at the same time to sufficient quantity of sterile saline solution to make, by thorough mixing, a thick paste. Lactic acid is added to lower the pH to 4.5 After through mixing, the encapsulated lactobacilli are added at room temperature. The lactobacilli were encapsulated by using the large scale method described as ENCAPSULATION METHOD E. The resultant mixture is then mixed with adequate magnesium sterate and silicon dioxide to render the mixture moldable and pressed into molds with eight pounds of moist pressure at 35°–38 degrees C. Usually, the concentration of magnesium stearate and silicon dioxide in the mixture to allow the foregoing is 0.01 to 0.1% by weight for each of the agents. This method provides stable suppositories, but the viability of the microorganisms varies from batch to batch.

SUPPOSITORY FORMULATION K, WITH SINGLE ANTIMICROBIAL AGENT:

Benzalkonium chloride (for a batch of 100 suppositories 12.5 grams) is added slowly while thoroughly stirring to a suspension of hydroxypropyl methyl cellulose (40 grams per batch of about 100 suppositories) and microcrystalline cellulose (20 grams per batch of about 100 suppositories) in sterile normal saline solution (quantity sufficient to make a thick paste, which is usually 120 ml.) at 35°–37 degrees C. The pH is slowly lowered to about 6.0–6.3 with reagent grade lactic acid. This step binds the antimicrobial to the base. The mixture is, at this point, a very thick paste in its consistency. After this step all operations are performed at 0–4 degrees C. The pH of the entire mixture is then lowered to 4.3–4.5 by addition of reagent grade lactic acid. Freshly obtained encapsulated lactobacilli bacteria are then added to achieve a final concentration of at least one million viable bacteria per suppository. Usually this requires addition of 4–6 fold excess of encapsulated bacteria (approximately 500 mg) because of losses which occur during the procedure. Quick and thorough mixing is important because the moisture adversely effects the viability of the organisms. The mixing can be done by spreading the paste in a thin layer on a sterile glass plate and then using a replicator to spread the bacteria evenly over the paste. Exposure to temperature at approximately 25 degrees or higher adversely affects the viability of bacteria in the suppository. Thereafter, about 2–4 grams each of magnesium stearate and silicon dioxide are added, with or without 2–3 grams of lactose. The materials are all thoroughly mixed at 0–4 degrees C. and then pressed into a mold and dried in a desiccating jar under vacuum at 0–4 degrees C. The suppositories are then sealed in air and moisture proof containers until used. During storage the suppositories should be protected from moisture and extreme temperature to ensure the viability of the lactobacilli.

SUPPOSITORY FORMULATION L WITH SINGLE ANTIMICROBIAL AGENT AND GLYCEROL BASE

Benzalkonium chloride (for a batch of 100 suppositories 12.5 grams) is added slowly while thoroughly stirring, to a suspension of glycerol at a concentration of 20– 80% in 1L of a sterile 0.15 normal saline solution. This step slightly thickens the mixture. The mixture, at this point is a thick and viscous suspension of thick honey like consistency. The pH of the entire mixture is then lowered to 4.3–4.5 with reagent grade lactic acid. The material is quickly cooled to 0–4 degrees C. and freshly obtained encapsulated lactobacilli bacteria are added. To achieve a minimum final concentration of one million viable bacteria per suppository, a 6–8 fold excess of encapsulated bacteria (approximately 600–800 mg) are added and blended in thoroughly together with 4–6 grams of lactose. The formulation at this stage is quite firm, like a soft wax at 0–4 degrees C., and can be easily pressed into a mold. The suppositories are then sealed in air and moisture proof containers until used.

LARGE BATCH FORMULATION M

Approximately 300 suppositories per pilot batch were made in accordance with this procedure, but the procedure can be used for a greater or smaller number as well. Sufficient quantities of benzalkonium chloride, imidiazolidinyl urea and diazolidinyl urea to achieve a final amount of 100 to 1,000 mg, 10 to 100 mg, and 10 to 100 mg, respectively, per suppository, as desired, are mixed together with sufficient quantities of nonoxynol 9 to achieve a final concentration of 90– 110 mg. of the latter in each suppository. The above ingredients are all added at the same time to sufficient quantity of sterile saline solution to make, by thorough mixing, a thick paste. In a representative embodiment 30 grams of benzalkonium chloride, 2.5 grams of imidiazolidinyl urea and 2.5 grams of diazolidinyl urea were added to approximately 50 ml of sterile saline solution at room temperature. Sufficient amount of ascorbic acid for 100 mg per suppository (a total of 30.0 grams) was then added, followed by the following materials: 140 grams of lactose (Fast Flow™) methyl cellulose (Methocel™) 2.5 grams, stearic acid 10 grams, sodium starch glycolate (Tabco™) 10 grams, sodium citrate 1.5 grams, silica 20–60 grams. After the foregoing materials were thoroughly mixed, the encapsulated lactobacilli (total of 3.0 grams) were added at room temperature. The lactobacilli were encapsulated substantially in accordance with Encapsulation Method B, described above. The resulting mixture was pressed into molds with gentile pressure at room temperature using a pill stamping machine.

IN VITRO AND IN VIVO BIOLOGICAL TESTING

The preferred embodiment of the vaginal suppository of the present invention having been made substantially in accordance with the procedures described in methods A or B, was tested for its effect on the following pathogenic organisms, and was found to be capable of killing these organisms in concentrations which are likely to be attained in vivo during normal intended use of the suppository.
BACTERIA: *Gardnerella vaginalis, Streptococcus pyogenes, Streptococcus agalactiae, Streptococcus faecalis, Staphylococcus aureus, Staphylococcus aureus* (Toxic Shock Toxin Production), *Neisseria gonorrhoeae, Escherichia coli, Klebsiella pneumoniae, Shigella dysenteriae, Salmonella typhi, Mycoplasma hominis, Mycoplasma pnumoniae, Ureaplasma urealyticum, Mobilluncus curtisii,* and *Chlymadia trachomatiis.*
VIRUSES: Human immunodeficiency virus, Herpes simplex I, Herpes simplex II, Cytomegalovirus (CMV), Hepatitis A, Hepatitis B
YEASTS: *Candida albicans, Candida parasolosis, Candida tropicalis, Candida glabrata, Candida psuedotropicalis*
TRICHOMONAS: *Trichomonas vaginalis*

In vitro and in vivo tests are further described as follows:
In the in vitro studies a volume of approximately 30 ml of the appropriate enriched media was used for introducing the particular pathogen to be tested against the antimicrobial effect of one suppository. Generally speaking, $10^6$ log phase pathogenic organisms were introduced into the media, this number being 2 or 3 orders of magnitude higher than a reasonable estimate of the number of pathogenic organisms (of one kind) to which a female may be exposed when having sexual intercourse with an infected male partner. The volume of 30 ml for one suppository was considered a dilution which was at least as much, or considerably greater than the dilution of the antimicrobial agents of one suppository in the vagina, after sexual intercourse. Accordingly, it is believed that as far as the number of pathogens and dilution of the antimicrobial agents are concerned, these tests were at least as rigorous or more rigorous than the conditions occurring in vivo, that is when the suppository of the invention is used in its intended manner.

*Gardnerella vaginalis*

In testing against *Gardnerella vaginalis*, $10^6$ viable organisms in duplicate from 300 clinical isolates (patients diagnosed with bacterial vaginosis) were added to enriched Mueller-Hinton broth. The suppositories of the invention, media and organisms were gently agitated at 37 degrees C. in a 10% $CO_2$ incubator. At 1, 2, and 3 hours an aliquot was plated quantitatively onto chocolate agar and incubated at 37 degrees in a 10% $CO_2$ incubator. The plates were read at 24, 48 and 72 hours. Results: Of the 300 clinical isolates of *Gardnerella vaginalis* tested under the above conditions against the suppository of the invention, there were no viable organisms found at the 1, 2, 3 or 4 hour sampling intervals.
*Streptococcus pyogenes, Streptococcus faecalis, Streptococcus agalactiae, Staphylococcus aureus* and toxigenic *Staphylococcus aureus*

Clinical isolates of *Streptococcus pyogenes, Streptococcus faecalis, Streptococcus agalactiae, Staphylococcus aureus* and toxigenic *Staphylococcus aureus* were obtained from gynecological patients using standard laboratory techniques. The clinical isolates $10^6$/ml (1 ml) were added in log phase to enriched Mueller-Hinton broth. The vaginal suppository of the invention, media, and organisms were gently agitated at 37 degrees C. in a 10% incubator. At 1, 2, and 3 hours an aliquot was plated quantitatively onto chocolate agar and inoculated at 37 degrees in a 10% $CO_2$ incubator. The plates were read at 24, 48, and 72 hours. Results: Of the clinical isolates of *Staphylococcus aureus, Streptococcus agalactiae, Streptococcus faecalis, Streptococcus pyogenes* and 30 clinical isolates of toxigenic *Staphylococcus aureus* none were found to be viable at the 1, 2, or 3 hour sampling periods.

Gram negative rods (bacteria)

Clinical isolates of *Escherichia coli* (100 isolates), *Klebsiella pneumoniae* (100 isolates), *Shigella dysenteriae* (30 isolates) and *Salmonella typhi* (30 isolates) were tested against the vaginal suppository of the present invention.

The clinical isolates $10^6$/ml (1 ml) were added to enriched Mueller-Hinton broth. The vaginal suppository of the invention, media, and organisms were gently agitated at 37 degrees C. in a 10% $CO_2$ incubator. At 1, 2, and 3 hours an aliquot was plated quantitatively onto chocolate agar and inoculated at 37 degrees in a 10% $CO_2$ incubator. The plates were read at 24, 48, and 72 hours. Results: Of the clinical isolates of *Escherichia coli, Klebsiella pneumoniae, Shigella dysenteriae,* and *Salmonella typhi* tested under the above conditions against the vaginal suppository of the present invention, there were no viable organisms found at the 1, 2, or 3 hour sampling intervals.

Yeasts

Clinical isolates of *Candida albicans* (100 isolates), *Candida parasolosis* (50 isolates), *Candida tropicalis* (50 isolates), *Candida glabrata* (50 isolates) and *Candida pseudotropicalis* (50 isolates) were obtained from gynecological patients with the clinical diagnosis of vaginitis.

The clinical isolates $10^6$/ml (1 ml) were added to enriched Mueller-Hinton broth. The vaginal suppository of the present invention, media, and organisms were gently agitated at 37 degrees C. in a 10% $CO_2$ incubator. At 1, 2, and 3 hours an aliquot was plated quantitatively onto chocolate agar and inoculated at 37 degrees in a 10% $CO_2$ incubator. The plates were read at 24, 48, and 72 hours. Results: Of the clinical isolates of *Candida albicans, Candida parasolosis, Candida tropicalis, Candida glabrata* and *Candida pseudotropicalis* tested under the above conditions against the suppository of the present invention, there were no viable organisms found at the 1, 2, or 3 hour sampling intervals.

*Trichomonas vaginalis*

Clinical isolates of *Trichomonas vaginalis* were obtained from gynecological patients with the clinical diagnosis of vaginitis.

The clinical isolates $10^6$/ml (1 ml) were added to enriched Feinstein-Weiberg media. The suppository of the present invention, media, and organisms were gently agitated at 37 degrees C. in a 10% $CO_2$ incubator. At 1, 2, and 3 hours an aliquot was added to additional Feinstein-Weiberg media quantitatively and incubated at 37 degrees in a 10% $CO_2$ incubator. The tubes were read at 24, 48 and 72 hours. Results: Of the 30 clinical isolates of *Trichomonas vaginalis* tested under the above conditions against the vaginal suppository of the present invention, there were no viable organisms found at the 1, 2, or 3 hour sampling intervals.

*Hemophilus ducreyii*

Clinical isolates (30) of *Hemophilus ducreyii* were obtained from patients diagnosed with *Hemophilus ducreyii* and from laboratory stocks.

The clinical isolates $10^6$/ml (1 ml) were added to enriched Mueller-Hinton media. The suppository of the present invention, media, and organisms were gently agitated at 37 degrees C. in a 10% $CO_2$ incubator. AT 1, 2, and 3 hours an aliquot was plated to additional enriched Mueller-Hinton chocolate agar quantitatively, and incubated at 37 degrees in a 10% $CO_2$ incubator. The plates were read at 24, 48, and 72 hours. Results: Of the clinical isolates of *Hemophilus ducreyii* tested under the above conditions against the suppository of the present invention, there were no viable organisms found at the 1, 2, or 3 hour sampling intervals.

*Neisseria gonorrhoeae*

One hundred (100) clinical isolates of *Neisseria gonorrhoeae* were obtained from gynecological patients with a clinical diagnosis of vaginitis or cervicitis.

The clinical isolates $10^6$/ml (1 ml) were added to enriched Mueller-Hinton broth. The suppository of the present invention, media, and organisms were gently agitated at 37 degrees C. in a 10% $CO_2$ incubator. At 1, 2, and 3 hours an aliquot was plated quantitatively onto chocolate agar and inoculated at 37 degrees in a 10% $CO_2$ incubator. The plates were read at 24, 48, and 72 hours. Results: Of the clinical isolates of *Neisseria gonorrhoeae* tested under the above conditions against the suppositories of the present invention, there were no viable organisms found at the 1, 2, or 3 hour sampling intervals.

Obligate Intracellular Pathogens

*Chlamydia trachomatis, Herpes simplex II*, and more recently *Human Immunodeficiency Virus* (HIV) are certainly among, if not the most significant sexually transmitted diseases. All of these pathogens are obligate, intracellular parasites and therefore, not amenable to the above described in vitro testing techniques with suppositories of the present invention. Moreover, antimicrobial, spermicidal and other substances in the suppositories affect tissue culture systems and this factor must be taken into consideration when the suppository of the present invention is tested against these pathogens. Thus, tests were performed in the following manner.

A suppository of the present invention was allowed to disintegrate in 30 ml of media and then added to either viral or chlamydial infective units ($10^6$) and incubated in a 10% $CO_2$ incubator for one hour at 37 degrees C. The cells were disrupted by sonication and then the entire 30c of material was centrifuged at 5000 ×g. Both the supernant and the sediment were inoculated into susceptible cell lines. The suppository of the present invention sterilized the *herpes simplex II, chlamydia trachomatis,* as well as HIV cultures by the one hour sampling interval.

IN VIVO AND IN VITRO COMBINATION STUDIES

A test was devised to measure the intra-vaginal pH and antimicrobial agent levels for several hours after administration of a single suppository of the present invention (prepared substantially in accordance with the procedure described in methods A and B. In the tests, vaginal pH was measured at time zero (0) and at hourly intervals up to eight hours after insertion of the suppository, and an aliquot of vaginal fluid was obtained from the posterior fornix at time 0 and at hourly intervals. The vaginal fluid aliquot was added to a lawn of pathogens or potential pathogens to determine how long the antimicrobial activity would persist intra-vaginally. Patients who had no signs or symptoms of any sexually transmitted disease as determined by a Gram stain, wet drop, and pH of vaginal fluid were selected for study. In this manner thirteen volunteer patients, twenty-one (21) to thirty-five (35) years of age were evaluated. After some experimentation, it was found that 200–300 µl of fluid from the posterior vaginal fornix could be removed serially using capillary attraction with a sterile Pasteur pipette.

Each volunteer was given one suppository at weekly intervals. Using this methodology, material adequate to study five to seven organisms could be obtained at each interval. It should be observed that during the study period (three weeks) the volunteers were required to refrain from sexual activity for at least five days prior to the day of the insertion of the suppository.

The vaginal pH, was measured by pH paper. A 10 µl aliquot of the vaginal fluid was applied to a freshly inoculated "lawn" (made with a "L glass rod") of each of the following organisms on enriched chocolate agar: *Gardnerella vaginalis, Streptococcus faecalis, Streptococcus pyogenes, Streptococcus agalactiae, Staphylococcus aureus, Staphylococcus aureus\** \*(toxic shock toxin producing); *Neisseria gonorrhoeae, Escherichia coli, Klebsiella pneumoniae, Shigella dysenteriae, Salmonella typhi; Candida albicans, Vandida parasolosis, Candida tropicalis, Candida pseudotropicalis,* and *Candida glabrata.* Results: The pH

*was maintained at* 4.5 for the test period. The above micro organisms were killed by the vaginal fluid aliquots for the entire study period.

In order to evaluate the prolonged effects of antimicrobial activity on viruses and *Chlamydia trachomatis* an aliquot of vaginal fluid obtained as above was added to 10 cc tubes containing susceptible cells and either *Chlamydia trachomatis, Herpes simplex* type II or HIV at $10^4$ infective units. This mixture was incubated for 1 hour. Then the cells were disrupted with sonic vibration and the supernatant material following centrifugation at 10,000×g was added to susceptible cells and incubated appropriately. Under these conditions, the *Chlamydia trachomatis* and viruses were completely destroyed.

EVALUATION OF THE SAFETY OF THE SUPPOSITORY OF THE PRESENT INVENTION USED DAILY FOR 60 DAYS

The purpose of this study was to evaluate the tolerance and any untoward effects relating to the use of the suppository of the present invention in healthy patients. In the study patients inserted one suppository of the invention daily for 60 days and reported any untoward effects of the use of the suppository which either the patient or their sexual partner may have experienced.

The clinical and subjective evaluation of these patients included the presence or absence of skin irritations, any untoward effects, increased discharge, changes in sensation, etc. and the appropriate microbiological examination for evaluation of the vaginal flora as well as the appropriate evaluation of their sexual partners, when appropriate to the study.

Only patients between eighteen (10) and forty-five (45) years of age, monogamous, with no gynecological problems of any kind, and using an acceptable method of contraception participated in this study. Patients were excluded from this study if they had any hypersensitivity to any of the study products, if they had any requirements for systemic or topical antimicrobials during the time of this study, if the patient had clinical or laboratory signs consistent with Candidasis, if the patient had lesions consistent with active *Herpes simplex* type II infection, if the patient had atrophic vaginitis, if the patient had cervicitis, or if the patient had signs or symptoms consistent with bacterial vaginosis.

RESULTS

Of the 103 women using the suppository of the present invention daily for sixty days, four reported mild irritation and three of them discontinued use of the product. Four patients reported complaints of irritation in their partners. No patients complained of changes in sensitivity, interference with their usual practices, or untoward discharge.

Thus, overall the suppository of the present invention was well tolerated in almost all of the study population. The higher acceptance of suppository of the invention vs. other types of barrier methods of contraception and prophylaxis can be attributed to several factors. These are: the suppositories of the invention disperse very rapidly. The excipient base of the suppository has affinity for the vaginal epithelium at the natural mildly acidic pH ranges that the lactic acid buffer system of the preferred embodiment maintains. Because of the affinity of the suppository's base to the vaginal epithelium, the antimicrobials, including the spermicide do not cause vaginal irritation. The suppository of the invention does not cause untoward discharge. Generally, in the preferred embodiment the suppository has a low mass of 2 grams compared to the usual 5 grams of many spermicidal preparations. Also, because of the rapid dispersing and adherence to the epithelium, it can be biodegraded rapidly.

Finally, there is a mild detergent action of the spermicide and some of the antimicrobial agents which helps decrease vaginal discharge. Additionally, the suppositories do not contain any lipids (oils, fats, etc.) but rather contain materials that adhere to the entire vaginal vault. Hence, there are no complaints of "messiness" with their use.

EVALUATION OF THE SAFETY OF THE SUPPOSITORY OF THE PRESENT INVENTION USED EVERY OTHER DAY FOR 60 DAYS

The purpose of this study was to evaluate the tolerance and any untoward effects of any kind relating to the use of the suppository of the present invention in healthy patients. In the study patients inserted a suppository of the invention every other day for a 60 day period and reported any untoward effects in themselves or their sexual partner.

The clinical and subjective evaluation included the presence of absence of skin irritations, any untoward effects, increased discharge, changes in sensation, etc. and the appropriate microbiological examination for evaluation of the vaginal flora as well as the appropriate evaluation of their sexual partners when appropriate to the study. Patients between eighteen (18) and forty-five (45) years of age, monogamous, with no gynecological problems of any kind, and using an acceptable method of contraception participated in this study.

Patients were excluded from this study for the same reasons which were reasons for exclusion in the study where patients used one suppository each day in a 60 day study period.

RESULTS

Of the 119 women using the suppository of the invention every other day, three (3) reported mild irritation. None of the sexual partners of the participants reported moderate or severe adverse reactions to the use of the product. Only six (6) patients complained of mild irritation in their partners. No patients complained of changes in sensitivity, interference with their usual practices, or abnormal discharge.

EFFECTS OF THE SUPPOSITORY OF THE INVENTION ON THE INCIDENCE OF SEXUALLY TRANSMITTED DISEASES

This study was designed to evaluate the safety and effectiveness of the suppository of the invention on preventing vaginal infections in non-monogamous patients. Patients were considered for entrance into this study if they stated they had four or more different sexual partners per year. Patients also had to use an effective form of contraception which was defined for the purposes of this study as an intra-uterine device (IUD), oral contraceptives, vaginal diaphragm, or cervical cap. The patient participants in the study were to be between eighteen (18) and forty-five (45) years of age and having regular menses.

In the study, the patients inserted a vaginal suppository of the present invention preferably five (5) but no sooner than two (2) minutes prior to sexual activity.

The patient participants were evaluated on the basis of their direct response relating to safety and efficacy. For example patients answered questions such as: Did you experience any burning, or tingling sensations, or hear of any similar problems from your partner? Any changes in sensation, also any effects on "hygienic" properties such as the presence of an untoward discharge after the use of the product were inquired of. Furthermore, patients provided an evaluation of their usual practices. The patients were be cultured at the time of entrance into the study to evaluate for the presence of yeast, *Neisseria gonorrhoeae, Chlamydia trachomatis, Gardnerella vaginalis* as well as a qualitative evaluation of their predominate vaginal bacterial flora.

Patients had a VDRL and HIV test at the beginning and at the conclusion of study. Also, patients underwent coloscopy at the beginning and end of the study to evaluate for the presence of Human Papilloma Virus (HPV). The duration of the study period was 6 months.

RESULTS:

Subjective Results: Of the 168 women studied, four complained of vaginal irritation, and two complained of irritation of their partner.

Clinical Results: Of the 168 women studied, none were found to have contracted *Neisseria gonorrhoeae*. The VDRL and HIV serologies remained negative. Four patients were fund to have contracted *Trichomonas vaginalis*, all of which were asymptomatic. Four patients were diagnosed with bacterial vaginosis. There were sixteen clinical outbreaks with *Herpes simplex* type II, in the forty-three patients with a prior history of *Herpes simplex* type II infections. There were no new primary cases of *Herpes simplex* type II in the study patients with no known previous history of *Herpes simplex* type II. No patient contracted *Chlamydia trachomatis*, lymphogranuloma venereum or granuloma inguinale.

All patients were colposcopically normal at the conclusion of the study. While this does not absolutely preclude against infection with HPV during the study, at least it precluded the advancement of the manifestations of HPV infection while using the suppository of the present invention.

In connection with this study it is noted that it is obviously difficult or impossible to quantitate the risk of and type of potential infection in non-monogamous persons without culturing the patient and her sexual partner prior to each exposure, which is, of course, impossible. Therefore, given the patients' prior histories as a control, it is clear that the use of the suppository of the invention prior to intercourse statistically and in actuality reduced the incidence of infection with sexually transmitted diseases in the study population. It is also noteworthy that those participants who did contract infection during the study admitted that they were "not sure" that they "always" used the suppository before sexual intercourse.

THE EFFECTS OF THE SUPPOSITORY OF THE PRESENT INVENTION ON RECURRENT MONILIA (YEAST) INFECTIONS

The purpose of this study was to investigate the safety and efficacy of the suppository of the present invention in preventing yeast infections in patients with histories of multiple vaginal yeast infections.

Patients with at least four different episodes of monilia infection quarterly for the previous year were included in this study. For the purpose of the study, each episode of yeast infection had to be preceded by at least one week of being totally asymptomatic (no complaints of puritis, infection or discharge). Furthermore, the most recent episode must have been followed by at least one week of being asymptomatic. Patients were between eighteen (18) and forty-five (45) years of age. Patients also had regular menstrual periods. Patients were excluded from the study if there was known any hypersensitivity to any of the ingredients in the study product. Patients were also excluded from the study if at the time of admission they had any symptoms either clinically and/or microbiologically of vulvo-vaginitis.

The patients were evaluated on the basis of their direct response to questions relating to safety and efficacy and clinical examinations. For example the questions were asked: Did you experience any burning, tingling sensations, or discharge from the use of the suppository? The duration of the study period was 6 months. Patients were cultured bimonthly if asymptomatic, and also at each episode of any vaginal symptomatology.

RESULTS: All patients tolerated the every other day usage of the suppository of the invention very well. The only complaints of irritation were caused by the yeast infections and during the symptom free intervals there were no complaints attributable to the use of the suppository.

Of the forty (40) patients that participated in this study thirteen (13) had four episodes of yeast infections, twelve (12) had three episodes of yeast infections, and fifteen (15) had two infections during the study period. Of the thirteen (13) patients who experienced four infections, four (4) were on cytotoxic drugs, two (2) on cytotoxic drugs and glucocorticosteriods, and four (4) on glucocorticosteriods. Additionally, four (4) patients had insulin dependent diabetes. three were also excessively obese, exceeding more than 50% over ideal body weight. Of the twelve (12) patients with three infection episodes, three (3) were on glucocorticosteriods, two (2) were on cytotoxic agents, tree (3) had insulin dependent diabetes, and four (4) were excessively obese.

Of the yeast species isolated from the one hundred eighteen episodes of infections, sixty were *Candida albicans*, eighteen (18) were *Candida globrata*, four (4) were *Candida tropicalis*, and three (3) were *Candida parasolosis*. The remainder had mixed infections with no significant differences between the respective infection rate groups.

DISCUSSION: The use of the suppository of the present invention every other day in patients with history of multiple yeast infections markedly reduced the incidence of recurrence in this patient population. Whereas it was not possible in this study group of patients with a history of recurrent infections to completely abolish the occurrence of yeast infections, the majority of patients who experienced three or four moniliasis were on cytotoxic agents and/or glucocorticosteriods. Additionally, the other metabolically adverse conditions such as diabetes or excessive obesity, no doubt, contributed to the recalcitrant nature of their problem with yeast infections.

Patients with no metabolic disorders, but who had so called environmental factors such as being very athletic and wearing tight and restrictive clothing had the lowest rate of infections.

Of interest was that all but five of these patients, within two weeks after the discontinuance of the suppository of the invention, no longer had lactobacilli as the predominate vaginal bacterial flora. These data mean that there are multiple factors involved in patients with recurrent episodes of yeast infections. At least one of these factors in patients with this problem seems to be the inability of lactobacilli to re-establish themselves as the predominate vaginal flora, and this factor is greatly and beneficially influenced with the vaginal suppository of the present invention.

What is claimed is:

1. A vaginal pessary comprising:

an effective amount of a pharmaceutically acceptable, topically usable antimicrobial agent;

at least approximately $10^3$ viable bacteria of the *lactobacillus acidophilus* species or of its *lactobacillus rhamnosus* variant, said bacteria being micro encapsulated whereby the bacteria stay viable during storage of the pessary in spite of presence of the antimicrobial agent, the substance providing the encapsulating coating for the bacteria being such that it releases bacteria upon prolonged exposure to moisture in the vaginal environment, and a pharmaceutically acceptable excipient thoroughly admixed with the antimicrobial agent and the micro encapsulated bacteria.

2. The vaginal pessary of claim 1 further comprising an effective amount of spermicidal agent.

3. The vaginal pessary of claim 1 further comprising an effective amount of a pharmaceutically acceptable buffer system that buffers the pH of the pessary in the range of 3.0 to 5.0.

4. The vaginal pessary of claim 3 wherein the buffering system buffers in the range of 4.3 to 4.5.

5. The vaginal pessary of claim 1 wherein the antimicrobial agent is selected from the group consisting of benzalkonium chloride, methylbenzethonium chloride, cetyl pyridinium chloride, alkyltrimethylammonium bromides, chlorhexidine gluconate and povidone iodine.

6. The vaginal pessary of claim 1 comprising a mixture of at least three antimicrobial agents, one of which is selected from the group consisting of benzalkonium chloride, methylbenzethonium chloride, cetyl pyridinium chloride, alkyltrimethylammonium bromides, chlorhexidine gluconate and povidone iodine, the other two antimicrobial agents being imidiazolidinyl urea and diazolidinyl urea.

7. The vaginal pessary of claim 1 wherein the *Lactobacillus acidophilus* or *Lactobacillus rhamnosus* bacteria are encapsulated in a sodium alginate coating.

8. The vaginal pessary of claim 1 wherein the *Lactobacillus acidophilus* or *Lactobacillus rhamnosus* bacteria are encapsulated in a acrylic methacrylic acid copolymer coating.

9. The vaginal pessary of claim 1 wherein the *Lactobacillus acidophilus* or *Lactobacillus rhamnosus* bacteria are encapsulated in a coating comprising polyvinylpyrrolidone and divinylbenzene.

10. The vaginal pessary of claim 1 wherein the *Lactobacillus acidophilus* or *Lactobacillus rhamnosus* bacteria are encapsulated in a coating comprising polyvinylpovidone.

11. The vaginal pessary of claim 1 further comprising an amount of ascorbic acid effective for increasing the viscosity of the cervical mucus.

12. A vaginal suppository comprising:
    an effective amount of a pharmaceutically acceptable, topically usable antimicrobial agent;
    at least approximately $10^3$ viable bacteria of the *Lactobacillus acidophilus* species or of its *Lactobacillus rhamnosus* variant, said bacteria being micro encapsulated whereby the bacteria stay viable during storage of the suppository in spite of presence of the antimicrobial agent, the substance providing the encapsulating coating for the bacteria being such that it releases bacteria upon prolonged exposure to moisture in the vaginal environment, and
    a pharmaceutically acceptable excipient thoroughly admixed with the antimicrobial agent and the micro encapsulated bacteria.

13. The vaginal suppository of claim 12 further comprising an effective amount of spermicidal agent selected from the group consisting of nonoxynol 9 or oxtoxynol 9.

14. The vaginal suppository of claim 13 further comprising an effective amount of a pharmaceutically acceptable buffer system that buffers the pH of the suppository in the range of 3.0 to 5.0.

15. The vaginal suppository of claim 14 wherein the buffering system buffers in the range of 4.3 to 4.5.

16. The vaginal suppository of claim 15 wherein the antimicrobial agent is selected from the group consisting of benzalkonium chloride, methylbenzethonium chloride, cetyl pyridinium chloride, alkyltrimethylammonium bromides, chlorhexidine gluconate and povidone iodine.

17. The vaginal suppository of claim 16 comprising a mixture of at least three antimicrobial agents, one of which is selected from the group consisting of benzalkonium chloride, methylbenzethonium chloride, cetyl pyridinium chloride, alkyltrimethylammonium bromides, chlorhexidine gluconate and povidone iodine, the other two antimicrobial agents being imidiazolidinyl urea and diazolidinyl urea.

18. The vaginal suppository of claim 17 comprising at least $10^6$ viable bacteria of the *lactobacillus acidophilus* species or of its *lactobacillus rhamnosus* variant.

19. The vaginal suppository of claim 18 wherein the *Lactobacillus acidophilus* or *Lactobacillus rhamnosus* bacteria are encapsulated in a sodium alginate coating.

20. The vaginal suppository of claim 18 wherein the *Lactobacillus acidophilus* or *Lactobacillus rhamnosus* bacteria are encapsulated in an acrylic methacrylic acid copolymer coating.

21. The vaginal suppository of claim 18 wherein the *Lactobacillus acidophilus* or *Lactobacillus rhamnosus* bacteria are encapsulated in a coating comprising polyvinylpyrrolidone and divinylbenzene.

22. The vaginal suppository of claim 18 wherein the *Lactobacillus acidophilus* or *Lactobacillus rhamnosus* bacteria are encapsulated in a coating comprising polyvinylpovidone.

23. The vaginal suppository of claim 12 wherein said anticrobial agent is selected from the group consisting of 12 to 3000 mg of benzalkonium chloride, 12 to 3000 mg of methylbenzethonium chloride, 25 to 4000 mg of cetylpyridinium chloride, 10 to 2000 mg of chlorhexidine gluconate, and 25 to 5000 mg of povidone iodine.

24. The vaginal suppository of claim 12 comprising approximately 10 to 1000 mg of imidiazolidinyl urea, or of diazolidinyl urea.

25. The vaginal suppository of claim 12 comprising approximately 50 to 500 mg of nonoxynol 9 or octoxynol 9.

26. The vaginal suppository of claim 12 further comprising an amount of ascorbic acid effective for increasing the viscosity of the cervical musus.

27. The vaginal suppository of claim 26 comprising 40–120 mg ascorbic acid.

28. A vaginal suppository comprising:
    an effective amount of a pharmaceutically acceptable, topically usable antimicrobial agent selected from the group consisting of benzalkonium chloride in the amount of 12 to 3000 mg, methylbenzethonium chloride in the amount of 12 to 3000 mg, cetyl pyridinium chloride in the amount of 25 to 4000 mg, alkyltrimethylammonium bromides in the amount of 25 to 4000 mg, chlorhexidine gluconate in the amount of 10 to 2000 mg, and povidone iodine in the amount of 25 to 5000 mg;
    10 to 1000 mg of imidiazolidinyl urea;
    10 to 1000 mg of diazolidinyl urea;
    a spermicidal agent selected from the group consisting of 50 to 500 mg of nonoxynol 9, and 50 to 500 mg of octoxynol 9;
    40 to 120 mg ascorbic acid;
    an effective amount of a pharmaceutically acceptable buffer system that buffers the pH of the suppository in the range of 4.3 to 4.5;
    at least approximately $10^3$ viable bacteria of the *Lactobacillus acidophilus* species or of its *Lactobacillus rhamnosus* variant, said bacteria being micro encapsulated whereby the bacteria stay viable during storage of the suppository in spite of presence of the antimicrobial agents, the substance providing the encapsulating coating for the bacteria being such that it releases bacteria upon prolonged exposure to moisture in the vaginal environment, and a pharmaceutically acceptable excipient thoroughly admixed with the antimicrobial agent and the micro encapsulated bacteria.

29. The vaginal suppository of claim 28 wherein the antimicrobial agent is benzalkonium chloride and where each suppository contains approximately 120 mg of benzalkonium chloride.

30. The vaginal suppository of claim 28 wherein the antimicrobial agent is cetylpyridinium chloride and where each suppository contains approximately 50 to 1000 mg of cetylpyridinium chloride.

31. The vaginal suppository of claim 28 wherein the antimicrobial agent is chlorhexidine gluconate and where each suppository contains approximately 25 to 1200 mg of chlorhexidine gluconate.

32. The vaginal suppository of claim 28 wherein the antimicrobial agent is povidone iodine and where each suppository contains approximately 120 mg of povidone iodine.

33. The vaginal suppository of claim 28 wherein the bacteria are *Lactobacillus rhamnosus,* and the bacteria are encapsulated in a coating selected from a group of micro encapsulating coatings which consists of sodium alginate coating, acrylic methacrylic acid copolymer coating, polyvinylpyrrolidone and divinylbenzene coating, and polyvinylpovidone coating.

34. The vaginal suppository of claim 30 having a total approximate mass of approximately 1.2 grams.

35. The vaginal suppository of claim 33 wherein the the pharmaceutically acceptable excipient is selected from the group consisting of hydroxy propyl methyl cellulose and silicon dioxide.

\* \* \* \* \*

UNITED STATES PATENT AND TRADEMARK OFFICE
CERTIFICATE OF CORRECTION

PATENT NO. : 5,466,463
DATED : November 14, 1995
INVENTOR(S) : Ford

It is certified that error appears in the above-identified patent and that said Letters Patent is hereby corrected as shown below:

Title page,
Line 9 of OTHER PUBLICATIONS, "nonoxynol-9" should be -- Nonoxynol-9 --.

Second column of OTHER PUBLICATIONS, "Lactosbacillus" should be -- Lactobacillus --.

Column 6,
Lines 46 and 56, "C." should be -- C --.

Column 7,
Lines 21 and 51, "C." should be -- C --.

Column 8,
Line 45, "C." should be -- C --.

Column 9,
Lines 16, 24, 27, 46 and 52, "C." should be -- C --.

Column 10,
Lines 32 and 46, delete "°" after "35".
Line 67, "C." should be -- C --.

Column 11,
Lines 17 and 23, "C." should be -- C --.

Column 12,
Lines 34 and 52, "C." should be -- C --.

UNITED STATES PATENT AND TRADEMARK OFFICE
CERTIFICATE OF CORRECTION

PATENT NO. : 5,466,463
DATED : November 14, 1995
INVENTOR(S) : Ford

It is certified that error appears in the above-identified patent and that said Letters Patent is hereby corrected as shown below:

<u>Column 13,</u>
Lines 2, 20, 36, 51 and 66, "C." should be -- C --.

Signed and Sealed this

Nineteenth Day of March, 2002

Attest:

JAMES E. ROGAN
*Director of the United States Patent and Trademark Office*

*Attesting Officer*